United States Patent [19]

Kraatz

[11] Patent Number: 5,679,796
[45] Date of Patent: Oct. 21, 1997

[54] PROCESS FOR THE PREPARATION OF 2-CHLORO-5-CHLOROMETHYLTHIAZOLE

[75] Inventor: Udo Kraatz, Leverkusen, Germany

[73] Assignee: Bayer Aktiengesellschaft, Leverkusen, Germany

[21] Appl. No.: 764,952

[22] Filed: Dec. 13, 1996

[30] Foreign Application Priority Data

Dec. 22, 1995 [DE] Germany .................. 195 48 417.7

[51] Int. Cl.⁶ ................................................. C07D 277/32
[52] U.S. Cl. .............................................................. 548/202
[58] Field of Search ................................................ 548/202

[56] References Cited

U.S. PATENT DOCUMENTS 4,748,243  5/1988  Beck .................................. 548/202

*Primary Examiner*—Robert Gerstl
*Attorney, Agent, or Firm*—Sprung Kramer Schaefer & Briscoe

[57] ABSTRACT

The invention relates to a novel process for the preparation of 2-chloro-5-chloromethylthiazole by reacting 5-methylene-1,3-thiazolidine-2-thiones with a chlorinating agent.

1 Claim, No Drawings

PROCESS FOR THE PREPARATION OF 2-CHLORO-5-CHLOROMETHYLTHIAZOLE

The invention relates to a novel process for the preparation of 2-chloro-5-chloromethylthiazole.

It is known that 2-chloro-5-chloromethylthiazole is obtained if allyl isothiocyanate (allyl mustard oil) of the formula (A) is reacted with a chlorinating agent in accordance with the following equation:

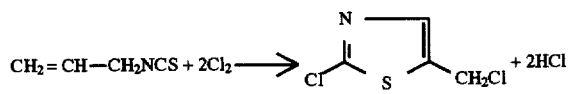

(cf. in this context EP-A 0260560).

It is also known that 2-chloro-5-chloromethylthiazole can be obtained if allyl isothiocyanates of the formula (B) are reacted with a chlorinating agent in accordance with the following equation:

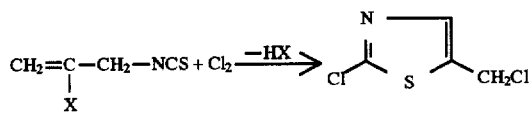

X=leaving group
(cf. in this context EP-A 0446913).

However, these processes are disadvantageous in that a considerable excess of chlorinating agent is used, it is necessary to work in a highly diluted system and the reaction temperature must be observed precisely.

Furthermore, the stable intermediate which forms in the course of the reaction must be converted into the desired end product in an additional reaction step, which is exothermic. This requires additional expenditure on monitoring, especially when the reaction is carried out on the industrial scale.

It has been found that 2-chloro-5-chloromethyl-thiazole of the formula (I)

is obtained in good yields and high purity if 5-methylene-1,3-thiazolidine-2-thiones of the formula (II)

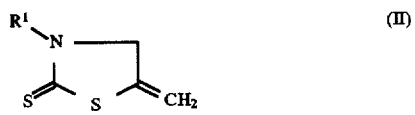

in which

R$^1$ represents hydrogen or the group R$^2$—CO—, in which

R$^2$ represents alkyl or optionally substituted phenyl, are reacted with a chlorinating agent, optionally in the presence of a diluent.

It is, surprisingly, possible in accordance with the process according to the invention to obtain the 2-chloro-5-chloromethyl-thiazole of the formula (I) in good yields and in high purity, despite the compulsory expectation from the prior art that under such mild chlorination conditions the >N-CS group would not be desulfurized (cf. e.g. Org. Synthesis 51,139 (1971). It was also not to be expected that the cyclic structure of the dithiocarbamate would be retained in the course of a chlorination (cf. e.g. Houben Weyl, Methoden der organischen Chemie, vol. 5/3, p. 648 (1962).

The reaction according to the invention therefore has the advantage of simple and rapid implementation, with high crude yields being obtained even without purification steps.

The nonappearance of a stable intermediate, in addition, does away with the subsequent thermolytic reaction step.

Using, for example, 5-methylene-1,3-thiazolidine-2-thione as starting material and elemental chlorine as chlorinating agent, the course of the reaction in the process according to the invention can be depicted by the following equation:

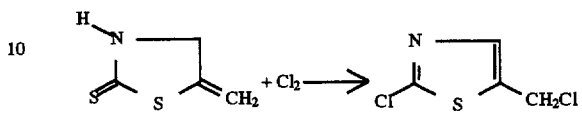

A general definition of the 5-methylene-1,3-thiazolidine-2-thiones to be used as-starting materials in the process according to the invention is given by the formula (II). In the formula (II), R$^1$ preferably represents hydrogen or the group R$^2$—CO—, in which R$^2$ preferably represents straight-chain or branched C$_1$–C$_4$-alkyl, such as in particular methyl, ethyl or isopropyl; and represents phenyl which is optionally substituted once to twice by identical or different substituents, of which methyl, ethyl, fluorine, chlorine, nitro and cyano may be mentioned.

The 5-methylene-1, 3-thiazolidine-2-thiones of the formula (II) are known in principle (cf. Liebigs Ann. Chem. 1985, 58 ff.).

Suitable chlorinating agents are elemental chlorine and compounds which give off chlorine under the reaction conditions, for example sulfuryl chloride or phosgene.

The process according to the invention is preferably carried out in the presence of a diluent.

Suitable diluents are customary organic solvents. These include, preferably, chlorinated aliphatic and aromatic hydrocarbons, such as dichloromethane, trichloromethane, trichloroethylene, tetrachloroethylene and carbon tetrachloride and, respectively, chlorobenzene or dichlorobenzene.

When carrying out the process according to the invention, the reaction temperatures can be varied within a relatively wide range. It is generally carried out at temperatures between −80° C. and 150° C., preferably at temperatures between −30° C. and 80° C.

The implementation of the reaction and working up are carried out in a generally customary manner (cf. also the Preparation Examples).

If a brominating agent is employed in the process according to the invention in place of a corresponding chlorinating agent, the 2-bromo-5-bromomethylthiazole of the formula (III)

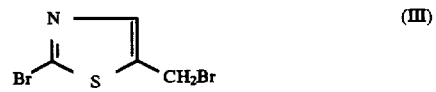

is obtained. The 2-bromo-5-bromomethylthiazole of the formula (III) is known(cf. EP-A 0376279).

The 2-chloro-5-chloromethylthiazole of the formula (I) which is to be prepared by the process according to the invention can be used as an intermediate in the preparation of biologically active compounds, for example insecticides (cf. e.g. EP-A 0192060).

PREPARATION EXAMPLES

Example 1

A stream of chlorine gas is passed at −10° C. into a suspension of 20 g (0.15 mol) of 5-methylene-1, 3-thiazolidine-2-thione in 200 ml of chloroform. After a short time, a clear solution is obtained which becomes cloudy as products precipitate out. As soon as chlorine is no longer taken up, the mixture is stirred at −10° C. for 10 minutes, the temperature is raised to 20° C. and the reaction mixture is washed a number of times with water. The solvent is then removed in vacuo.

26.9 g of yellow, liquid crude product are obtained with a GC purity of 87%, corresponding to a theoretical yield of 92.8%.

The crude product can be purified still further by chromatography from silica gel in the chloroform/ethyl acetate (4:1) system.

10.6 g (GC purity >99%) of 2-chloro-5-chloromethylthiazole of melting point 32° C. are obtained.

Example 2

Chlorine gas is passed at 0° C. (for 15 minutes) into a solution of 2.6 g (0.015mol) of 3-acetyl-5-methylene-1,3-thiazolidine-2-thione in 50 ml of chloroform. The mixture is then subsequently stirred at 20° C. for 20 minutes, the solution is washed twice with water and the organic phase is concentrated after drying it over magnesium sulfate.

A crude yield of 2.4 g is obtained as a yellow oil which, according to GC analysis, contains 41% of the desired 2-chloro-5-chloromethyl-1,3-thiazole.

I claim:

1. Process for the preparation of 2-chloro-5-chloromethylthiazole of the formula (I)

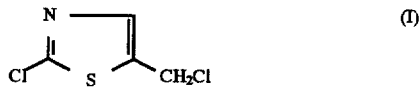

characterized in that 5-methylene-1,3-thiazolidine-2-thiones of the formula (II)

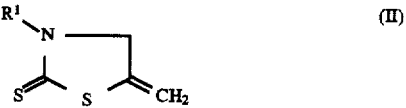

in which $R^1$ represents hydrogen or the group $R^2$—CO—, in which $R^2$ represents alkyl or optionally substituted phenyl, are reacted with a chlorinating agent, optionally in the presence of a diluent.

* * * * *

Adverse Decisions in Interference

In the designated interferences involving the following patents, final decisions have been rendered that the respective patentees are not entitled to patents containing the claims listed.

Patent No. 5,679,796, Udo Kraatz, PROCESS FOR THE PREPARATION OF 2-CHLORO-5-CHLOROM-ETHYLTHIAZOLE, Interference No. 105,277, final judgment adverse to the patentees rendered May 5, 2006, as to claim 1.

*(Official Gazette August 8, 2006)*